(12) United States Patent
Miln et al.

(10) Patent No.: US 9,839,218 B2
(45) Date of Patent: Dec. 12, 2017

(54) PESTICIDAL COMPOSITION

(75) Inventors: Colin D Miln, Greensboro, NC (US);
Ravi Ramachandran, Guelph (CA);
Giulia Capuzzi, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 651 days.

(21) Appl. No.: 13/519,922

(22) PCT Filed: Dec. 28, 2010

(86) PCT No.: PCT/US2010/062220
§ 371 (c)(1),
(2), (4) Date: Dec. 13, 2012

(87) PCT Pub. No.: WO2011/082162
PCT Pub. Date: Jul. 7, 2011

(65) Prior Publication Data
US 2013/0210627 A1    Aug. 15, 2013

Related U.S. Application Data

(60) Provisional application No. 61/290,683, filed on Dec. 29, 2009.

(51) Int. Cl.
| | |
|---|---|
| *A01N 43/40* | (2006.01) |
| *A01N 37/34* | (2006.01) |
| *A01N 37/40* | (2006.01) |
| *A01N 25/04* | (2006.01) |
| *A01N 37/10* | (2006.01) |
| *A01N 37/44* | (2006.01) |
| *A01N 39/02* | (2006.01) |
| *A01N 39/04* | (2006.01) |
| *A01N 43/42* | (2006.01) |
| *A01N 43/653* | (2006.01) |
| *A01N 43/90* | (2006.01) |

(52) U.S. Cl.
CPC ............. *A01N 43/40* (2013.01); *A01N 25/04* (2013.01); *A01N 37/10* (2013.01); *A01N 37/34* (2013.01); *A01N 37/40* (2013.01); *A01N 37/44* (2013.01); *A01N 39/02* (2013.01); *A01N 39/04* (2013.01); *A01N 43/42* (2013.01); *A01N 43/653* (2013.01); *A01N 43/90* (2013.01)

(58) Field of Classification Search
CPC ........ A01N 43/40; A01N 37/10; A01N 37/34; A01N 43/653; A01N 43/90; A01N 37/40; A01N 25/04; A01N 25/30
USPC ..................... 504/130, 139, 141, 144, 145
See application file for complete search history.

(56) References Cited

U.S. PATENT DOCUMENTS

| | | | | |
|---|---|---|---|---|
| 4,108,629 | A * | 8/1978 | McKendry ............. | A01N 43/40 504/255 |
| 5,175,353 | A | 12/1992 | Jones et al. | |
| 5,374,603 | A * | 12/1994 | Mulqueen .............. | A01N 43/40 504/130 |
| 6,827,478 | B2 | 12/2004 | Becker et al. | |
| 2007/0237956 | A1 | 10/2007 | Figuly et al. | |
| 2008/0004182 | A1 | 1/2008 | Linton et al. | |
| 2008/0194408 | A1* | 8/2008 | Ramachandran ...... | A01N 25/30 504/140 |
| 2009/0054239 | A1* | 2/2009 | Hopkins ................ | A01N 43/40 504/255 |
| 2009/0306003 | A1 | 12/2009 | Kabanov et al. | |

FOREIGN PATENT DOCUMENTS

DE    WO 2006/029736 A1 *    3/2006    ............. A01N 25/02

* cited by examiner

*Primary Examiner* — John Pak
*Assistant Examiner* — Nathan W Schlientz
(74) *Attorney, Agent, or Firm* — R. Kody Jones

(57) ABSTRACT

Stable, single-phase pesticidal emulsifiable concentrates are provided which comprise (a) a pesticide mixture comprising a major amount of a water-insoluble pesticide and a minor amount of a water-soluble pesticidal salt; (b) a solvent system comprising (i) a major amount of an organic solvent comprising at least one non aqueous polar solvent; and (ii) a minor amount of water; and, optionally, (c) an emulsifying surfactant system enabling an oil in water emulsion to be formed when the concentrate formulation is diluted upon addition to water.

13 Claims, No Drawings

PESTICIDAL COMPOSITION

This application is a 371 of International Application No. PCT/US2010/062220 filed Dec. 28, 2010, which claims priority to U.S. 61/290,683 filed Dec. 29, 2009, the contents of which are incorporated herein by reference.

The present invention relates to pesticidal emulsifiable concentrates, to the preparation thereof and to a method of using such compositions to control pests in crops of useful plants.

Emulsifiable concentrate (EC) formulations are favored liquid delivery systems for agriculturally active compounds. As a rule, conventional ECs contain at least one active ingredient, one or more surfactants which act as emulsifiers upon dilution of the EC with water, and a water immiscible solvent having a low solubility in water and that is capable of dissolving a wide range of active ingredients. Typical ECs contain little or no water as higher levels of water can cause phase inversion and cream separation.

Due to the presence of the solvent, many pesticides formulated as an EC have advantages such as a higher degree of systemicity and higher overall activity compared to the same pesticide formulated as a water dispersible granule (WG) or as oil in water emulsion (EW).

In some cases it may be desirable to combine different pesticides to provide a single formulation taking advantage of the additive properties of each separate pesticide in order to optimize biological performance. Also, transportation and storage costs can be minimized by preparing an EC in which the concentration of the pesticides is as high as is practicable and in which any desired adjuvants are "built-in" to the formulation as opposed to the separate pesticide products and adjuvants being tank-mixed by an end user.

However, when pesticide products are combined that have significantly different physical, chemical or biological properties, such as where one pesticide is a water insoluble solid and the other pesticide is a water soluble salt (available, for example, as an aqueous SL formulation), the greater is the probability that the stability of an EC premix formulation prepared there from may be disturbed, or that one or more components may separate out from the EC. This is particularly true when there are substantial amounts of water present in the commercially available forms of an individual pesticide component that is used to make an EC premix.

Considering the variety of conditions and special situations under which pesticides are stored, shipped and used around the world, there remains a need for EC premix formulations of pesticides that provide stability benefits under at least some of those conditions and situations. There is a further need for EC premix formulations which can be readily prepared from commercially available aqueous pesticide components.

SUMMARY OF THE INVENTION

Stable, single-phase pesticidal emulsifiable concentrates are provided which comprise (a) a pesticide mixture comprising a major amount of at least one water-insoluble pesticide and a minor amount of at least one water-soluble pesticidal salt; (b) a solvent system comprising (i) a major amount of an organic solvent comprising at least one non aqueous polar solvent; and (ii) a minor amount of water; and, optionally, (c) an emulsifying surfactant system enabling an oil in water emulsion to be formed when the concentrate formulation is diluted upon addition to water. In one embodiment, the water is present in the concentrate in an amount greater than 3% by weight of the entire composition. The EC compositions of the invention can be used directly or with dilution to control weeds and other pests in crops of useful plants.

In accordance with the invention, it has been found that stable, single-phase pesticidal emulsifiable concentrates of a first substantially water-insoluble pesticide and a second water-soluble pesticidal salt can be prepared by adding an aqueous solution of the second water-soluble pesticide salt to a non-aqueous solution of the first water-insoluble pesticide and the emulsifying surfactant system. The water-soluble pesticide is dissolved along with the water-insoluble pesticide and other ingredients within the continuous single phase system of the novel emulsifiable concentrate of the invention which has practical utility in terms of storage, shipment and use.

The non aqueous polar solvent or solvent mixture can be chosen such that a cloudy oil in water emulsion is formed when the concentrate is diluted into water to form an aqueous spray solution, wherein the emulsion droplets will have an average particle size in excess of 10 nm.

The present invention also includes a method for controlling pests such as weeds at a locus such as soil or foliage where crops of useful plants are being grown or on areas in which it is intended to grow those cultivated plants which comprises treating said locus with an emulsifiable concentrate according to the invention or emulsifying a concentrate according to the present invention in water and treating said locus with the obtained diluted aqueous emulsion.

DETAILED DESCRIPTION OF THE INVENTION

In an EC composition of the present invention, at least one water-insoluble pesticide is combined with at least one water-soluble, salt-forming pesticide in a solvent system comprising a major amount of an organic component comprising at least one non aqueous polar solvent and a minor amount of water. The EC composition may contain any combination of such water-insoluble and water-soluble pesticides provided that the at least one water-insoluble pesticide is present in a major amount relative to the water-soluble pesticide and, in addition, the EC is a stable, single phase composition. The non aqueous polar solvent, in addition to providing its customary function as a carrier, operates to compatibilize the pesticide mixture into a stable, single phase solution.

A pesticide as defined herein includes any chemical classified as a pesticide or active ingredient (a.i.) by any regulatory authority; for example in the United States by the Environmental Protection Agency (EPA). Generally, a pesticide is a chemical which, when applied in a pesticidally sufficient amount to a susceptible plant, animal and/or microorganism and/or to the locus thereof, kills, inhibits or alters the growth of the plant, animal and/or microorganism. Included non-restrictively among pesticides are herbicides, fungicides, insecticides, acaricides, nematicides, molluscicides and plant and insect growth regulators as well as crop enhancers The term "major amount" as used herein generally means a predominant amount, while a "minor amount" refers to an amount less than a major amount as defined herein. More specifically, the term "major amount" when used with reference to the solvent system means at least 75 wt. % and the term "minor amount" means less than 25 wt. % of the solvent system; more particularly, "major amount" means at least 80% and "minor amount" less than 20%; most particularly, "major amount" means at least 90% and "minor amount" less than 10% by weight of the solvent system. When used in reference to the weight ratio of water-insoluble pesticide(s) to water-soluble pesticidal salt(s), major amount:minor amount means a ratio of from 10:1 to 1.01:1.

The term "stable" as used herein with reference to a pesticidal EC of the invention means meeting or exceeding the performance under test of commercial standard formulations at ambient storage temperature with respect to formulation homogeneity and dispersability, and when the respective EC has passed the heat stability test (Test 2) and cold stability test (Test 3) as provided in the examples.

The term single-phase as used herein denotes that the pesticides (a) are completely dissolved in the homogenous mixture of (a), (b) and optionally (c), without any phase separation, such as by passing the single phase solution test (Test 1) as provided in the examples.

As used herein, the term "Hansen Solubility Parameter" refers to the system of describing solute solubility in a solvent based on the nonpolar parameter, polar parameter, hydrogen bonding parameter, and total solubility parameter. See pages 4-6 of "Hansen Solubility Parameters" by Charles M. Hansen, ISBN0-8493-7248-8. For definition of Hh=Hydrogen Bonding Solubility Parameter see page 17 of the above book. For definition of Hp=Polar Solubility Parameter see page 16-17 of the above book.

Accordingly, in one embodiment, the stable, single-phase pesticidal emulsifiable concentrate compositions of the present invention comprise
a) a pesticide mixture comprising a major amount of at least one water-insoluble pesticide and a minor amount of at least one water-soluble pesticidal salt;
b) a solvent system comprising (i) a major amount of an organic solvent comprising at least one non aqueous polar solvent; and (ii) a minor amount of water; and, optionally,
c) an emulsifying surfactant system enabling an oil in water emulsion to be formed when the concentrate formulation is diluted upon addition to water.

In one embodiment, water-insoluble pesticides are those which are substantially water-insoluble. More specifically, substantially water-insoluble pesticides are those which have solubility in water of less than or equal to 200 mg/l; more particularly a solubility in water of less than or equal to 100 mg/l. In one embodiment, suitable water soluble pesticides are those which have solubility in water of less than or equal to 20 mg/l.

Examples of suitable water-insoluble pesticides include esters of fluoroxypyr, esters of bromoxynil, esters of MCPA, pinoxaden, clodinafop, cyhalofop, diclofop, diclofop-p, fenoxaprop, fenoxaprop-p, fluazifop, fluazifop-p, haloxyfop, haloxyfop-p, propaquizafop, quizalofop, quizaolofop-p, esters of 2,4-D and propiconazole.

In one embodiment, suitable water-insoluble pesticides are herbicides including esters of fluoroxypyr and esters of bromoxynil. A particularly suitable ester of fluoroxypyr is fluoroxypyr meptyl ester (commercially available for manufacturing use only as Starane F technical).

In an embodiment, water-insoluble pesticides that are solid are optionally milled to the desired particle size. For example, the solid may be milled in a dry state using an air-mill or other suitable equipment, or it may be milled in the water-immiscible solvent with solvent-soluble surfactants as necessary, to achieve the desired particle size. In one embodiment, the particle size may be an average particle size of about 0.2 to about 20 microns, suitably about 0.2 to about 15 microns, more suitable about 0.2 to about 10 microns.

Suitable water-soluble pesticides useful in the EC of the present invention include herbicides which are salts of 3,6-dichloro-2-methoxybenzoic acid (dicamba), 2,4-D, clomeprop; dichlorprop; MCPA; MCPB; mecoprop; mecoprop-P; chloramben; TBA, picloram, clopyralid or aminopyralid.

In one embodiment, the water-soluble pesticide salt is a 2,4-D, MCPA or dicamba salt which is selected from sodium, potassium, ammonia, dimethylamine, diethylamine, triethylamine, monoethanolamine, diethanolamine, 2-hydroxyethylammonium, aminoethoxyethanol, triisopropanolamine, tris(2-hydroxypropyl)amine, aminopropylmorpholine and triethanolamine. More specifically, the dicamba salt is the aminoethoxyethanol salt of dicamba which is commercially available as Vanquish® herbicide.

In one embodiment, the pesticide mixture (a) of the inventive EC comprises (1) at least one water-soluble synthetic auxin herbicide such as, for example, 2,4-D, clomeprop; dichlorprop; MCPA; MCPB; mecoprop; mecoprop-P; chloramben; TBA, picloram, clopyralid or aminopyralid, (2) at least one water-insoluble graminicide such as, for example, pinoxaden, clodinafop, cyhalofop, diclofop, diclofop-p, fenoxaprop, fenoxaprop-p, fluazifop, fluazifop-p, haloxyfop, haloxyfop-p, propaquizafop, quizalofop, quizaolofop-p and (c), optionally, a fungicide such as propiconazole.

In another embodiment, the water-insoluble pesticide is at least one pesticide selected from pinoxaden, fenoxaprop-p, clodinafop and propiconazole.

In an embodiment, the emulsifiable concentrate is prepared by combining an aqueous solution of the water-soluble pesticide salt with a non-aqueous solution of the water-insoluble pesticide and, optionally, at least a portion of the emulsifying surfactant system.

In another embodiment, the weight ratio of water-insoluble pesticide to water-soluble pesticidal salt in the EC of the present invention is from 10:1 to 1.01:1, particularly from 5:1 to 1.01:1 and most particularly from 2:1 to 1.01:1.

In the context of the present invention, non-aqueous, polar solvents suitable for use in the solvent system include those having a Hansen polarity parameter greater than 2, in particular greater than 5 and more particularly between 5 and 15.

Examples of suitable non-aqueous, polar solvents include acetone, amyl acetate, butanol, benzyl alcohol, cetyl alcohol, dimethyl ether, dipropylene glycol, diethylene glycol monomethyl ether, octanol, hallcomid M-8-10, hexylene glycol, cyclohexanol, ethyl lactate, ethyl alcohol, 2-ethyl hexanol, glycerol monoacetate, glycerol diacetate, glycerol triacetate, 3-hexenol, n-hexyl alcohol, isopropyl myristate, lactic acid, lactic acid 2-ethyl hexyl ester, lactic acid n-propyl ester, methyl alcohol, methyl n-amyl ketone, methyl isobutyl ketone, oleyl alcohol, propanol, tetrahydrofurfuryl alcohol, butyrolactone, chlorobenzene, diacetone alcohol, n-decanol, N,N-dimethyl decanamide, N,N-dimethyl octanamide, dimethyl lactamide, n-decyl alcohol, dipropyleneglycol monomethylether, ethylene glycol monobutyl ether, isobornyl acetate, isobutyl alcohol, mesityl oxide, methyl ethyl ketone, 2-methyl-2,4-pentanediol, N-octyl pyrrolidone, N-methylpyrrolidone, n-octyl alcohol, oxo-decyl acetate, oxo-heptyl acetate, oxo-hexyl acetate, oxo-nonyl acetate, oxo-octyl acetate, oxo-tridecyl acetate, propyleneglycol monomethyl ether, triethylene glycol, triethyl phosphate, lactic acid n-butyl ester, lactic acid ethyl ester, dodecyl pyrrolidone, N,N-dimethyl acetamide, propylene carbonate and mixtures thereof.

In one embodiment, the non-aqueous, polar organic solvent component of the solvent system comprises a solvent or mixture of solvents having a polarity (Hp) of from 4 to 12 and a hydrogen bonding value (Hh) of from 7 to 20. In this regard, the polar organic solvent component can comprise a solvent mixture which has a polarity and hydrogen bonding value within the specified range. In addition to the polar solvents listed above, other polar solvents which may be included in such polar organic solvent mixtures are propylene glycol, acetophenone, cyclohexanone, dimethyl sulfoxide, ethylene glycol and methylcyclohexanone.

In one embodiment, in addition to the non-aqueous polar solvent, the organic solvent component of the solvent system (b) includes at least one solvent that is substantially immiscible with water. Suitable water immiscible organic solvents include aromatic hydrocarbons and mixtures of aromatic hydrocarbons such as the petroleum derived aromatic solvents. Particular examples of suitable aromatic hydrocarbon solvents include Aromatic 100, Aromatic 150, Aromatic 200 or the naphthalene depleted (ND) or ultra low naphthalene (ULN) variants thereof, commercially available from Exxon Mobil Chemical of Houston, Tex.

In an embodiment, the solvent system (b) of the emulsifiable concentrate according to the invention also contains a minor amount of water wherein the water content is greater than 3% by weight, in particular greater than 5% by weight, more particularly between 5% and 15% by weight, and most particularly between 5% and 10% by weight of the entire composition.

The presence of surfactants is not required in order to successfully combine the aqueous solution of the water soluble herbicidal salt and the water insoluble (oil soluble) herbicide into a single phase homogeneous EC in accordance with the invention. However, in practice, an emulsifying surfactant system in an amount sufficient to facilitate emulsification of the concentrate on preparation by the end-user of a dilute aqueous sprayable composition will be either be tank-mixed by an end user or, more typically, will be"built-in" to the EC for convenience.

Accordingly, in an embodiment, in addition to the pesticide mixture (a) and the solvent system (b), the single-phase pesticidal emulsifiable concentrate compositions of the present invention comprise an emulsifying surfactant system (c).

In one embodiment, the emulsifying surfactant system (c) comprises at least one alkyl polyglycoside surfactant.

Exemplary alkyl polyglycosides include AGNIQUE® PG ("APG") 8107 (Cognis Corporation, Cincinnati, Ohio) (an alkyl polyglycoside in which the alkyl group contains 8 to 10 carbon atoms and has an average degree of polymerization of 1.7), AGNIQUE®PG 9116 (Cognis Corporation, Cincinnati, Ohio) (an alkyl polyglycoside in which the alkyl group contains 9 to 11 carbon atoms and has an average degree of polymerization of 1.6) and AGNIQUE® PG 8105 (Cognis Corporation, Cincinnati, Ohio) (an alkyl polyglycoside in which the alkyl group contains 8 to 10 carbon atoms and has an average degree of polymerization of 1.5).

In another embodiment, the emulsifying surfactant system (c) comprises at least one alkylene oxide surfactant. The alkylene oxide surfactants are suitably ethylene oxide adducts; more particularly, the surfactant is an ethylene oxide adduct containing at least one mole of propylene oxide.

In another embodiment, the emulsifying surfactant system (c) comprises a mixture of at least one alkyl polyglycoside and at least one propylene-oxide/ethylene-oxide copolymer.

In an embodiment, suitable co-polymers of ethylene oxide and propylene oxide can be di- and tri-block copolymers, such as ABA or BAB block copolymer or BA block copolymers. Examples include the GENAPOL PF series (CLARIANT), the PLURONIC series (BASF), the SYNPERONIC PE series (UNIQEMA), or the TOXIMUL series (STEPAN). A preferred group of ethylene oxide/propylene oxide block copolymers for use in the compositions of this invention are butyl based poly(oxypropylene) poly(oxyethylene) block copolymers having an average molecular weight in a range of 2,400 to 3,500 (e.g. TOXIMUL 8320, Stepan Chemical Co.). Suitable examples include Pluronic L10, Pluronic L44, Pluronic L63, Pluronic L64, Pluronic P84, Pluronic P104, Pluronic P105, Step-Flow 26, Toximul 8323, and Toximul 8320.

In another embodiment, a cloudy oil in water emulsion is formed when the EC of the present invention is added to water. Such an emulsion will have a volume-weighted median diameter as measured by diffraction light scattering in excess of 10 nm, particularly from 10 nm to 10 microns and most particularly from 100 nm to 1micron.

Further aspects of the invention include a method of preventing or combating infestation of crop plants by weed pests, by diluting an amount of an EC of the invention with a suitable liquid carrier (in particular an aqueous liquid carrier), such as water or liquid fertilizer, and applying a herbicidally effective amount of the dilute composition to the plant or locus as desired. The compositions of the present invention may also be combined in a continuous flow apparatus with water in spray application equipment, such that no holding tank is required for the diluted product.

The inventive EC compositions can be stored conveniently in a container from which it is poured, or pumped, or into which a liquid carrier is added prior to application.

The advantages of the EC compositions of the present invention include: storage-stability for extended periods, for example 6 months or longer at room temperature; simple handling is made possible for users because dilution is made with water, or other liquid carrier, for preparation of application mixtures; the emulsions are not susceptible to coalescence when dilution is made with fertilizer solutions for preparation of application mixtures.

The invention relates also to herbicidal compositions obtained by diluting a herbicidal EC of the present invention in a suitable carrier, such as water or liquid nitrogen fertilizer, such that the final concentration of the herbicides present is between about 0.01% and about 10% of active ingredient (a.i.).

As used herein, the term "herbicidally effective amount" is that amount of herbicide sufficient for controlling or modifying plant growth. Controlling or modifying effects include all deviation from natural development, for example, killing, retardation, leaf burn, albinism, dwarfing and the like. The term "plant(s)" refers to all physical parts of a plant, including seeds, seedlings, saplings, roots, tubers, stems, stalks, foliage and fruits. The term "locus" refers to where the undesired plant or weed is growing or is expected to grow, including crop areas which are areas of land on which the cultivated useful plants are already growing or in which the seeds of those cultivated plants have been sown, and also areas of land on which it is intended to grow those cultivated plants.

The selection of application rates and methods relative to providing a desired level of herbicidal activity for a composition of the invention is routine for one of ordinary skill in the art. More specifically, the components used in the EC composition of the invention can be applied in a variety of ways known to those skilled in the art, at various concentrations. The rate of application of the compositions of the invention will depend on a number of factors including, for example, the herbicides chosen for use, the identity of the plants whose growth is to be controlled, the degree of control required, the formulations selected for use, whether the compound is to be applied for foliage or root uptake, level of weed pressure, plant conditions, the timing and method of application, weather and growing conditions as well as the activity of the herbicidally active ingredients and any applicable label rate restrictions.

In an embodiment, target weeds include, for example, the broadleaf weeds such as those for cereal crops including, for example, those species listed on the current product labels for products containing actives such as the aminoethoxyethanol salt of dicamba) (Vanquish®) or fluoroxypyr meptyl ester (Starane®) which product labels are incorporated by reference herein.

The composition according to the invention is suitable for all methods of application conventionally used for herbicides in agriculture such as pre- or post-emergence applications to crop areas. For example, the compositions of the invention may be mixed with water and/or fertilizers and may be applied pre-emergence and/or post-emergence to a desired locus by any means, such as airplane spray tanks, direct injection spray equipment, knapsack spray tanks, farm equipment used in ground spraying (e.g., boom sprayers, hand sprayers), and the like.

As a general guide, an application rate of from 1 to 3000 g active ingredient per hectare is suitable, in particular from 50 to 500 g active ingredient per hectare. In one embodiment, suitable rates for the herbicides used in the inventive compositions are comparable to the existing rates given on the current product labels for products containing such actives. For example, Starane® brand of fluoroxypyr meptyl can be applied at a rate of from 207-409 g a.i./hectare (144-284 g acid equivalent) and Vanquish® or Clarity® brand of dicamba aminoethoxyethanol salt can be applied at a rate of from 330-2650 g/ha (224-1796 acid equivalent).

In one embodiment, the invention also relates to a method for preventing or controlling weeds in crops of useful plants, said method comprising treating the plants, plant parts or locus thereof with a herbicidally effective amount of the inventive EC or dilute herbicidal spray compositions as described herein. For example, the invention relates to a method for preventing or controlling weeds in crops of useful plants, said method comprising forming a dilute herbicidal spray composition comprising combining the EC of the present invention with a suitable carrier, such as water or liquid nitrogen fertilizer, in an amount sufficient to obtain the desired final concentration of each of the herbicides (typically a herbicidally effective amount) and treating the desired crop area, such as plants, the plant parts or the locus thereof, with said dilute composition.

The EC compositions according to the invention and the dilute spray compositions prepared there from are suitable for combating and/or preventing weeds in crops of useful plants. In one embodiment, particularly suitable crops of useful plants are the cereal crops including wheat, oats, barley and rye. "Crops" are to be understood also to include those crops that have been made tolerant to pests and pesticides, as a result of conventional methods of breeding or by genetic engineering.

Crops are to be understood as also including those crops which have been rendered tolerant to herbicides or classes of herbicides (e.g. ALS-, GS-, EPSPS-, PPO-, ACCase and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful crop plants include ornamental plants such as flowers or bushes, and turf grasses, for example, in golf-courses, lawns, parks and roadsides, or those grown commercially for sod.

Other active ingredients such as herbicides, plant growth regulators, algicides, fungicides, bactericides, viricides, insecticides, acaricides, nematicides or molluscicides may be present in the emulsifiable concentrates of the present invention or may be added as a tank-mix partner to the dilute spray compositions prepared there from.

In addition, the EC compositions of the invention may further comprise other additives. Such additives include safeners, thickeners, flow enhancers, wetting agents, anti-foaming agents, biocides, buffers, chelating agents, lubricants, fillers, drift control agents, deposition enhancers, evaporation retardants, frost protecting agents, insect attracting odor agents, UV protecting agents, fragrances, and the like. The thickener may be a compound that is soluble or able to swell in water, such as, for example, polysaccharides of xanthans (e.g., anionic heteropolysaccharides), alignates, guars or celluloses such as RHODOPOL® 23 (Xantham Gum) (Rhodia Inc., Cranbury, N.J.); synthetic macromolecules, such as polyethylene glycols, polyvinyl pyrrolidones, polyvinyl alcohols, polycarboxylates of swellable structure-forming silicates such as pyrogenic or precipitated silicic acids, bentonites, montmorillonites, hectonites, or attapulgites; or organic derivatives of aluminum silicates. The frost protecting agent may be, for example, ethylene glycol, propylene glycol, glycerol, diethylene glycol, triethylene glycol, tetraethylene glycol, urea, or mixtures thereof. Representative antifoam agents are silica, polydialkylsiloxanes, in particular polydimethylsiloxanes, fluoroaliphatic esters or perfluoroalkylphosphonic/perfluoroalkylphosphinic acids or the salts thereof and mixtures thereof. Preferred are polydimethylsiloxanes, such as Dow Corning® Antifoam A. Representative biocides include 1,2-benzisothiazolin-3-one, available as PROXEL® GXL (Arch Chemicals).

The EC compositions of the invention may be mixed with fertilizers and/or adjuvants such as non-ionic surfactants, crop oil concentrates or methylated esters of vegetable oils. Representative adjuvants include, but are not limited to, SCORE® adjuvant and TURBOCHARGE® adjuvant, both available from Syngenta Crop Protection Canada. The fertilizers may comprise, for example, either nitrogen based such as 28-0-0 or 30-0-0 or nitrogen, phosphorous, and/or potassium. In one embodiment, the fertilizer may be 10-34-0 fertilizer.

The emulsifiable concentrates of the present invention can be prepared by combining an aqueous solution of the water-soluble herbicide salt with a non-aqueous solution of the water-insoluble herbicide and, optionally, at least a portion of the emulsifying surfactant system.

In one embodiment, the emulsifiable concentrate is prepared by first charging a vessel with a non-aqueous organic solvent and adding a pre-heated water-insoluble herbicide such as Fluoroxypyr meptyl ester to the solvent and mixing until homogeneous. Secondly, pre-heated emulsifiers along with the non-aqueous polar solvent are added and agitated until the components are fully mixed. Finally, an aqueous solution of a water-soluble herbicide salt such as Dicamba-DGA salt is added to the solvent solution and the resulting solution is stirred until uniform.

The following examples illustrate further some of the aspects of the invention but are not intended to limit its scope. Where not otherwise specified throughout this specification and claims, percentages are by weight.

Example 1

402.5 g of Fluoroxypyr methyl heptyl ester (meptyl ester) was melted and then added to 597.5 g of Aromatic 150ND to create a 40% w/w solution of Fluoroxypyr meptyl ester. 33.5 g of Pluronic P105 was then added to 265.3 g of this 40% Fluoroxypyr meptyl solution. To a separate vessel, 141.4 g of Dicamba diglycolamine aqueous salt solution (approximately 38.5% w/w Dicamba acid, 56.8% Dicamba-DGA salt) was added. To this, 161.5 g of ethyl lactate and 67 g of Agnique PG8107 were added and dissolved. The Fluoroxypyr meptyl solution noted above (298.8 g) was then added to this separate vessel containing the aqueous Dicamba salt solution and the mixture agitated until dissolution to produce a single phase solution. 1 g of antifoam (Agnique DFM 114FS) was then added to this product. Upon mixing a homogeneous liquid was obtained. When the product is added to water it forms a cloudy emulsion (5 g product into 95 g water).

TABLE 1

| Components | Wt(g) | % w/w |
| --- | --- | --- |
| Aromatic 150ND | 158.5 | 23.7% |
| Fluroxypyr meptyl ester | 106.8 | 15.95% |
| Pluronic P105 | 33.5 | 5.0% |
| Dicamba-DGA salt | 80.32 | 12.0% |
| Water | 61.08 | 9.1% |
| Ethyl lactate | 161.5 | 24.1% |
| Agnique PG8107 | 67 | 10.0% |
| Antifoam | 1 | 0.15% |
| Total | 669.7 g | 100% |

Example 2

15.25 g of Fluoroxypyr meptyl ester was melted and added to 24.35 g of Aromatic 150ND to produce a ~38% w/w Fluoroxypyr meptyl solution. To this solution, Pluronic P105 (5 g) was added and dissolved. To a separate vessel 21.1 g of Dicamba diglycolamine aqueous salt solution was added (approximately 38.5% Dicamba acid, 56.8% Dicamba-DGA salt). To this separate vessel 10 g of Agnique PG8107 and 24.1 g of Dipropylene glycol monomethylether were added and dissolved. The oil solution of Fluoroxypyr meptyl (44.6 g) noted above was then added to the aqueous Dicamba salt solution (55.2 g) with agitation and rapidly dissolved. To this, 0.1 g of Silex SE-2 antifoam and 0.1 g of further water were added. Upon mixing a homogeneous liquid was obtained. When this product was diluted in water (5 g product into 95 g water) a cloudy emulsion was formed.

TABLE 2

| Components | Wt(g) | % w/w |
| --- | --- | --- |
| Aromatic 150ND | 24.35 | 24.35% |
| Fluroxypyr meptyl ester | 15.25 | 15.25% |
| Pluronic P105 | 5.0 | 5.0% |
| Dicamba-DGA salt | 11.98 | 11.98 |
| Water | 9.22 | 9.22% |
| Dipropylene glycol monomethylether | 24.1 | 24.1% |
| Agnique PG8107 | 10 | 10.0% |
| Antifoam | 0.1 | 0.1% |
| Total | 100 g | 100% |

Example 3

402.5 g of Fluoroxypyr methyl heptyl ester (meptyl ester) was melted and then added to 597.5 g of Aromatic 150ND to create a 40% w/w solution of Fluoroxypyr meptyl ester. 5 g of Pluronic P105 was then added to 39.6 g of this 40% Fluoroxypyr meptyl ester solution followed by 24.1 g of tetrahydrofurfuryl alcohol and 0.2 g of antifoam (Agnique DFM 114FS). To this solution 10 g of Agnique PG8107 was added, followed by 21.1 g of Dicamba diglycolamine aqueous salt solution (approximately 38.5% w/w Dicamba acid (acid equivalent—AE), 56.8% Dicamba-DGA salt) was added. Upon mixing a homogeneous liquid was obtained. When this product was diluted in water (5 g product into 95 g water) a cloudy emulsion was formed.

TABLE 3

| Components | Wt(g) | % w/w |
| --- | --- | --- |
| Aromatic 150ND | 23.66 | 23.66% |
| Fluroxypyr meptyl ester | 15.94 | 15.94% |
| Pluronic P105 | 5.0 | 5.0% |
| Dicamba-DGA salt | 11.98 | 11.98% |
| Water | 9.12 | 9.12% |
| Tetrahydrofurfuryl alcohol | 24.1 | 24.1% |
| Agnique PG8107 | 10 | 10.0% |
| Antifoam | 0.2 | 0.1% |
| Total | 100 g | 100% |

In the following illustrative Examples, test methods for various parameters were as follows:
Test 1—Single Phase Solution At the end of the procedure used to prepare the final concentrated pesticidal product mixture (e.g., as outlined in Example 1) agitation was stopped and the mixture allowed to come to rest at room temperature (20-25° C.) for a period of at least 30 minutes. The static mixture was then evaluated visually for the presence of a single phase homogenous solution at room temperature (20-25° C.). Examples of unacceptable non single phase behaviour would be the visual presence of solids or the visual presence of two distinct liquid phases.

Test 2—Heat Stability

An aliquot of the final concentrated pesticidal product mixture (e.g. 50 mls from Example 1) was placed in a sealed, transparent container and stored (unagitated) at 50° C. for 2 weeks after which time it was evaluated visually for the presence of a single phase homogeneous solution. Examples of non single phase behavior would be the visual presence of solids or the visual presence of two distinct liquid phases.

Test 3—Cold Stability

An aliquot of the final concentrated pesticidal product mixture (e.g. 50 mls from Example 1) was placed in a sealed, transparent container and stored (unagitated) at 0° C. for 2 weeks after which time it was evaluated visually for the presence of a single phase homogeneous solution. Examples of non single phase behavior would be the visual presence of solids or the visual presence of two distinct liquid phases.

Examples 4-8

Following procedures similar to examples 1-3, a series of emulsifiable concentrates were prepared using various amounts of dicamba DGA as water-soluble pesticide and bromoxynil octanoate or fluoroxypyr meptyl ester as water-insoluble pesticide. The role of the polar solvent in the emulsifiable concentrate was investigated, with DPM (Dipropyleneglycol monomethylether) being used as the polar solvent in examples 4-7, but not included in example 8 in order to measure the effect on phase homogeneity.

The examples further illustrate that the presence of surfactants is not required to successfully combine the pesticide components into a single phase homogeneous product. Accordingly, this shows that the single-phase emulsifiable concentrate (EC) of the invention is not related to micro-emulsifiable concentrates (MEC's) since MEC's rely on surfactants for compatibilization. Surfactants, however, are necessary in order to form a successful emulsion once the EC product is diluted in water (Test 4).

TABLE 4

| Example | Water soluble AI | Wt (g) | Water Insoluble AI | Wt (g) | Polar Solvent | Wt (g) | Co-solvent | Wt (g) | Surfactants | Wt (g) | Test 1 | Test 2 | Test 3 | Test 4 |
|---|---|---|---|---|---|---|---|---|---|---|---|---|---|---|
| 4 | Dicamba-DGA (38.5% AE, 56.8% as salt) | 21.1 | Bromoxynil octanoate (92.7% w/w) | 15.25 | DPM | 60 | Aromatic 200ND | 24.35 | — | — | Yes | Yes | Yes | No |
| 5 | Dicamba-DGA (38.5% AE, 56.8% as salt) | 10.55 | Bromoxynil octanoate (92.7% w/w) | 7.625 | DPM | 30 | Aromatic 200ND | 12.175 | APG 8107U/ Pluronic P105 | 7.1/3.55 | Yes | Yes | Yes | Yes |
| 6 | Dicamba-DGA (38.5% AE, 56.8% as salt) | 10.55 | Fluroxypyr meptyl ester (98%) | 7.625 | DPM | 12.05 | Aromatic 150ND | 12.175 | — | — | Yes | Yes | Yes | No |
| 7 | Dicamba-DGA (38.5% AE, 56.8% as salt) | 10.55 | Fluroxypyr meptyl ester (98%) | 7.625 | DPM | 12.05 | Aromatic 150ND | 12.175 | APG 8107U/ Pluronic P105 | 5/2.5 | Yes | Yes | Yes | Yes |
| 8 | Dicamba-DGA (38.5% AE, 56.8% as salt) | 10.55 | Fluroxypyr meptyl ester (98%) | 7.625 | No polar solvent added | 0 | Aromatic 150ND | 12.175 | APG 8107U/ Pluronic P105 | 5/2.5 | No | n/a | n/a | n/a |

Test 4—Emulsion Formation and Stability

An aliquot of the final concentrated pesticidal product mixture (e.g. 5 g from Example 1) was added to 50 ppm water (e.g. ~95 mls of water if 5 g of product were used). The water was contained in a glass cylinder which, following product addition was stopped and inverted through 15 complete inversions (each inversion lasting ~2 s). A visual observation was recorded as to whether the emulsion was cloudy or not. Examples of non cloudiness would be a completely transparent solution or a mostly transparent solution with visible oil droplets present and would indicate that a stable emulsion was not formed.

In the following illustrative Examples, a "Y" or "Yes" in connection with a particular formulation example indicates that such example passed a particular test and an "N" or "No" in connection with a particular formulation example indicates that such formulation example failed a particular test.

Examples 9-10

Following procedures similar to examples 1-3, emulsifiable concentrates were prepared using dicamba DGA as water-soluble pesticide and bromoxynil octanoate or fluoroxypyr meptyl ester as water-insoluble pesticide. The particle size of emulsion droplets formed when an EC in accordance with the present invention is diluted in water was investigated. In general, ECs will have an average particle size (Dv50) of greater than 10 nm (particle size determined after dilution of EC (5% w/v in 50 ppm water). These examples demonstrate that the compatibilizing effect provided by an EC according to the invention is not related to the production of a micro-emulsifiable concentrate (MEC) since MEC's are typically quoted as having approximately 10 nm particle size (Source: ISBN 0-471-49883-1 "Surfactants and Polymers in Aqueous Solution", Holmberg et al, p. 139, 2nd Edition). Furthermore micro-emulsions produce a transparent product on dilution in water. These examples produce a cloudy emulsion on dilution in water. (THFA=Tetrahydrofurfuryl alcohol

TABLE 5

| Example | Water soluble AI | Wt (g) | Water Insoluble AI | Wt (g) | Polar Solvent | Wt (g) | Co-solvent | Wt (g) | Surfactants | Wt (g) | Test 1 | Test 2 | Test 3 | Test 4 | Dv50 |
|---|---|---|---|---|---|---|---|---|---|---|---|---|---|---|---|
| 9 | Dicamba-DGA (38.5% AE, 56.8% as salt) | 21.1 | Bromoxynil octanoate | 15.25 | DPM | 60 | Aromatic 200ND | 24.35 | APG 8107U/ Pluronic P105 | 5/2.5 | Yes | Yes | Yes | Yes | 500 nm |
| 10 | Dicamba-DGA (38.5% AE, 56.8% as salt) | 2.76 | Fluroxypyr meptyl ester | 2 | THFA | 12.04 | Aromatic 150ND | 3.2 | APG 8107U/ Pluronic P105 | 5/2.5 | Yes | Yes | Yes | Yes | 400 nm |

Examples 11-38

Following procedures similar to examples 1-3, a series of emulsifiable concentrates were prepared using dicamba DGA as water-soluble pesticide and bromoxynil octanoate or fluoroxypyr meptyl ester as water-insoluble pesticide. The role of various polar solvents in the emulsifiable concentrate was investigated. The examples in Table 6 demonstrate that a range of polar solvents are suitable for use in the present invention.

TABLE 6

| Example | Water soluble AI | Wt (g) | Water Insoluble AI | Wt (g) | Polar Solvent | Wt (g) | Co-solvent | Wt (g) | Surfactants | Wt (g) | Test 1 | Test 2 | Test 3 |
|---|---|---|---|---|---|---|---|---|---|---|---|---|---|
| 11 | Dicamba-DGA (38.5% AE, 56.8% as salt) | 21.1 | Bromoxynil octanoate (92.7% w/w) | 15.25 | DPM | 60 | Aromatic 200ND | 24.35 | — | — | Yes | Yes | Yes |
| 12 | Dicamba-DGA (38.5% AE, 56.8% as salt) | 2.76 | Fluroxypyr meptyl ester (98% w/w) | 2 | THFA | 12.04 | Aromatic 150ND | 3.2 | — | — | Yes | Yes | Yes |
| 13 | Dicamba-DGA (38.5% AE, 56.8% as salt) | 2.76 | Fluroxypyr meptyl ester | 2 | THFA | 12.04 | Aromatic 150ND | 3.2 | APG 8107U/ Pluronic P105 | 5/2.5 | Yes | Yes | Yes |
| 14 | Dicamba-DGA (38.5% AE, 56.8% as salt) | 2.76 | Fluroxypyr meptyl ester | 2 | Benzyl Alcohol | 12.04 | Aromatic 150ND | 3.2 | APG 8107U/ Pluronic P105 | 5/2.5 | Yes | Yes | Yes |
| 15 | Dicamba-DGA (38.5% AE, 56.8% as salt) | 2.76 | Fluroxypyr meptyl ester | 2 | Dimethyl lactamide | 12.04 | Aromatic 150ND | 3.2 | — | — | Yes | Yes | Yes |
| 16 | Dicamba-DGA (38.5% AE, 56.8% as salt) | 2.76 | Fluroxypyr meptyl ester | 2 | Dimethyl lactamide | 13.04 | Aromatic 150ND | 4.2 | APG 8107U/ Pluronic P105 | 5/2.5 | Yes | Yes | Yes |
| 17 | Dicamba-DGA (38.5% AE, 56.8% as salt) | 2.76 | Fluroxypyr meptyl ester | 2 | Ethyl Lactate | 12.04 | Aromatic 150ND | 3.2 | — | — | Yes | Yes | Yes |
| 18 | Dicamba-DGA (38.5% AE, 56.8% as salt) | 2.76 | Fluroxypyr meptyl ester | 2 | Ethyl Lactate | 12.04 | Aromatic 150ND | 3.2 | APG 8107U/ Pluronic P105 | 5/2.5 | Yes | Yes | Yes |

TABLE 6-continued

| Example | Water soluble AI | Wt (g) | Water Insoluble AI | Wt (g) | Polar Solvent | Wt (g) | Co-solvent | Wt (g) | Surfactants | Wt (g) | Test 1 | Test 2 | Test 3 |
|---|---|---|---|---|---|---|---|---|---|---|---|---|---|
| 19 | Dicamba-DGA (38.5% AE, 56.8% as salt) | 2.76 | Fluroxypyr meptyl ester | 2 | Hallcomid M-8-10 | 12.04 | Aromatic 150ND | 3.2 | APG 8107U/ Pluronic P105 | 5/2.5 | Yes | Yes | Yes |
| 20 | Dicamba-DGA (38.5% AE, 56.8% as salt) | 2.76 | Fluroxypyr meptyl ester | 2 | DPM | 12.04 | Aromatic 150ND | 3.2 | — | — | Yes | Yes | Yes |
| 21 | Dicamba-DGA (38.5% AE, 56.8% as salt) | 2.76 | Fluroxypyr meptyl ester | 2 | Hexylene Glycol | 12.04 | Aromatic 150ND | 3.2 | APG 8107U/ Pluronic P105 | 5/2.5 | Yes | Yes | Yes |
| 22 | Dicamba-DGA (38.5% AE, 56.8% as salt) | 2.76 | Fluroxypyr meptyl ester | 2 | Cyclohexanol | 12.04 | Aromatic 150ND | 3.2 | APG 8107U/ Pluronic P105 | 5/2.5 | Yes | Yes | Yes |
| 23 | Dicamba-DGA (38.5% AE, 56.8% as salt) | 2.76 | Bromoxynil Octanoate | 2 | DPM | 12.04 | Aromatic 150ND | 3.2 | — | — | Yes | Yes | Yes |
| 24 | Dicamba-DGA (38.5% AE, 56.8% as salt) | 2.76 | Bromoxynil Octanoate | 2 | DPM | 12.04 | Aromatic 150ND | 3.2 | APG 8107U/ Pluronic P105 | 5/2.5 | Yes | Yes | Yes |
| 25 | Dicamba-DGA (38.5% AE, 56.8% as salt) | 2.76 | Bromoxynil Octanoate | 2 | Ethyl Lactate | 12.04 | Aromatic 150ND | 3.2 | — | — | Yes | Yes | Yes |
| 26 | Dicamba-DGA (38.5% AE, 56.8% as salt) | 2.76 | Bromoxynil Octanoate | 2 | Ethyl Lactate | 12.04 | Aromatic 150ND | 3.2 | APG 8107U/ Pluronic P105 | 5/2.5 | Yes | Yes | Yes |
| 27 | Dicamba-DGA (38.5% AE, 56.8% as salt) | 2.76 | Bromoxynil Octanoate | 2 | THFA | 12.04 | Aromatic 150ND | 3.2 | — | — | Yes | Yes | Yes |
| 28 | Dicamba-DGA (38.5% AE, 56.8% as salt) | 2.76 | Bromoxynil Octanoate | 2 | THFA | 12.04 | Aromatic 150ND | 3.2 | APG 8107U/ Pluronic P105 | 5/2.5 | Yes | Yes | Yes |
| 29 | Dicamba-DGA (38.5% AE, 56.8% as salt) | 2.76 | Bromoxynil Octanoate | 2 | Benzyl Alcohol | 12.04 | Aromatic 150ND | 3.2 | — | — | Yes | Yes | Yes |
| 30 | Dicamba-DGA (38.5% AE, 56.8% as salt) | 2.76 | Bromoxynil Octanoate | 2 | Diethylene glycol monomethyl ether | 12.04 | Aromatic 150ND | 3.2 | — | — | Yes | Yes | Yes |

TABLE 6-continued

| Example | Water soluble AI | Wt (g) | Water Insoluble AI | Wt (g) | Polar Solvent | Wt (g) | Co-solvent | Wt (g) | Surfactants | Wt (g) | Test 1 | Test 2 | Test 3 |
|---|---|---|---|---|---|---|---|---|---|---|---|---|---|
| 31 | Dicamba-DGA (38.5% AE, 56.8% as salt) | 2.76 | Bromoxynil Octanoate | 2 | Octanol | 12.04 | Aromatic 150ND | 3.2 | — | — | Yes | Yes | Yes |
| 32 | Dicamba-DGA (38.5% AE, 56.8% as salt) | 2.76 | Bromoxynil Octanoate | 2 | Octanol | 12.04 | Aromatic 150ND | 3.2 | APG 8107U/ Pluronic P105 | 5/2.5 | Yes | Yes | Yes |
| 33 | Dicamba-DGA (38.5% AE, 56.8% as salt) | 2.76 | Bromoxynil Octanoate | 2 | Hallcomid M-8-10 | 12.04 | Aromatic 150ND | 3.2 | — | — | Yes | Yes | Yes |
| 34 | Dicamba-DGA (38.5% AE, 56.8% as salt) | 2.76 | Bromoxynil Octanoate | 2 | Hallcomid M-8-10 | 12.04 | Aromatic 150ND | 3.2 | APG 8107U/ Pluronic P105 | 5/2.5 | Yes | Yes | Yes |
| 35 | Dicamba-DGA (38.5% AE, 56.8% as salt) | 2.76 | Bromoxynil Octanoate | 2 | Hexylene Glycol | 12.04 | Aromatic 150ND | 3.2 | — | — | Yes | Yes | Yes |
| 36 | Dicamba-DGA (38.5% AE, 56.8% as salt) | 2.76 | Bromoxynil Octanoate | 2 | Hexylene Glycol | 12.04 | Aromatic 150ND | 3.2 | APG 8107U/ Pluronic P105 | 5/2.5 | Yes | Yes | Yes |
| 37 | Dicamba-DGA (38.5% AE, 56.8% as salt) | 2.76 | Bromoxynil Octanoate | 2 | Cyclohexanol | 12.04 | Aromatic 150ND | 3.2 | — | — | Yes | Yes | Yes |
| 38 | Dicamba-DGA (38.5% AE, 56.8% as salt) | 2.76 | Bromoxynil Octanoate | 2 | Cyclohexanol | 12.04 | Aromatic 150ND | 3.2 | APG 8107U/ Pluronic P105 | 5/2.5 | Yes | Yes | Yes |

Examples 39-41

Following procedures similar to examples 1-3, a series of emulsifiable concentrates were prepared using dicamba DGA (38.5% AE, 56.8% as salt) as water-soluble pesticide and bromoxynil octanoate or fluoroxypyr meptyl ester as water-insoluble pesticide. The role of weight ratio between water insoluble (or oil soluble) pesticide to the pesticidal salt (water soluble a.i.) was investigated. The following examples illustrate a weight ratio range for the water insoluble (or oil soluble) herbicide to the herbicidal salt (water soluble a.i.) of from 10:1 to 1.01:1. This data provides examples at 1.2:1, 4:1 and 8:1 which is within a weight ratio of from 10:1 to 1.01:1.

TABLE 7

| Examples | Water soluble AI | Wt (g) | Oil Soluble AI | Wt (g) | AI ratio | Polar Solvent | Wt (g) | Co-solvent | Wt (g) | Surfactants | Wt (g) | T1 | T2 | T3 | T4 |
|---|---|---|---|---|---|---|---|---|---|---|---|---|---|---|---|
| 39 | Dicamba-DGA | 6 | Bromoxynil octanoate (92.7% w/w) | 15.25 | 4:1 | DPM | 24.2 | Aromatic 150ND | 24.35 | APG 8107/ Pluronic P105 | 10/5 | Yes | Yes | Yes | Yes |
| 40 | Dicamba-DGA | 3 | Bromoxynil octanoate (92.7% w/w) | 15.25 | 8:1 | DPM | 24.2 | Aromatic 150ND | 24.35 | APG 8107/ Pluronic P105 | 10/5 | Yes | Yes | Yes | Yes |

TABLE 7-continued

| Examples | Water soluble AI | Wt (g) | Oil Soluble AI | Wt (g) | AI ratio | Polar Solvent | Wt (g) | Co-solvent | Wt (g) | Surfactants | Wt (g) | T1 | T2 | T3 | T4 |
|---|---|---|---|---|---|---|---|---|---|---|---|---|---|---|---|
| 41 | Dicamba-DGA | 10.55 | Fluroxypyr meptyl ester (98% w/w) | 7.625 | 1.2:1 | DPM | 12.05 | Aromatic 150ND | 12.175 | APG 8107U/ Pluronic P105 | 5/2.5 | Yes | Yes | Yes | Yes |

Examples 42-49

Following procedures similar to examples 1-3, a series of emulsifiable concentrates were prepared using dicamba, MCPA, or 2,4-D as water-soluble pesticide and bromoxynil octanoate or fluoroxypyr meptyl ester as water-insoluble pesticide. The role of various salts was investigated. The following examples illustrate a range of active ingredients that can be used in accordance with the present invention. Suitable aqueous solutions of herbicidal salts include: Dicamba-DGA (38.5% AE, 56.8% as salt), Dicamba-DMA, Dicamba-K, MCPA-DMA and 2,4-D amine.

TABLE 8

| Example | Water soluble AI | Wt (g) | Water Insoluble AI | Wt (g) | Polar Solvent | Wt (g) | Co-solvent | Wt (g) | Surfactants | Wt (g) | Test 1 |
|---|---|---|---|---|---|---|---|---|---|---|---|---|
| 42 | Dicamba-DGA | 10.55 | Bromoxynil octanoate | 7.625 | DPM | 30 | Aromatic 200ND | 12.175 | APG 8107U/ Pluronic P105 | 7.1/3.55 | Yes |
| 43 | Dicamba-DGA | 21.1 | Bromoxynil octanoate | 15.25 | DPM | 60 | Aromatic 200ND | 24.35 | — | — | Yes |
| 44 | Dicamba-DGA | 10.55 | Fluroxypyr meptyl Ester | 7.625 | DPM | 12.05 | Aromatic 150ND | 12.175 | APG 8107U/ Pluronic P105 | 5/2.5 | Yes |
| 45 | MPCA-DMA (24% AE) | 2 | Fluroxypyr meptyl Ester | 6.4 | DPM | 33.8 | Aromatic 200ND | 21.3 | — | — | Yes |
| 46 | MPCA-DMA (24% AE) | 8 | Bromoxynil octanoate | 1.54 | DPM | 13.46 | — | — | — | — | Yes |
| 47 | 2.4-D amine (600 g/L) | 1 | Bromoxynil octanoate | 1.54 | DPM | 21.46 | — | — | — | — | Yes |
| 48 | Dicamba-DMA (30.5% AE) | 6.5 | Bromoxynil octanoate | 1.54 | DPM | 13.46 | — | — | — | — | Yes |
| 49 | Dicamba-K (36% AE) | 6.3 | Bromoxynil octanoate | 1.54 | DPM | 13.46 | — | — | — | — | Yes |

Examples 50-53

Following procedures similar to examples 1-3, a series of emulsifiable concentrates were prepared using three active ingredients (a.i.). The use of a $3^{rd}$ a.i. which can be either water soluble (e.g. MCPA amine) or water insoluble/oil soluble (e.g. MCPA 2EHE or Bromoxynil Octanoate) was investigated. Dicamba-DGA=(38.5% AE, 56.8% as salt); MCPA 2EHE=MCPA 2-ethylhexyl ester; MCPA amine=MCPA dimethylamine salt (aqueous solution (24% AE, 33% as salt); In Example: 50% Water=5%=[5.19×(100−56.8)]/(5.19+3.75+10.9+16.5+6+2.46+1.23)=2.24/46.03; In Example 51: % Water=5%=[5.19×(100−56.8)]/(5.19+3.75+8.7+13.5+6+2.46+1.23)=2.24/40.83; In Example 52: % Water=16%=[[5.19×(100−56.8)]+[14.5×(100−33)]]/(5.19+3.75+5.43+14.5+37+6+2.46+1.23)=(2.24+9.715)/75.56; In Example 53: % Water=5%=[[5.19×(100−56.8)]/(5.19+3.75+1+30.55+6)=2.24/46.49.

TABLE 9

| Example | Water soluble AI | Wt (g) | Water Insoluble AI | Wt (g) | 3rd AI | Oil/Water Soluble (3rd AI) | Wt (g) | Polar Solvent | Wt (g) | Co-solvent | Wt (g) | Surfactants | Wt (g) | 1 | 2 | 3 | 4 |
|---|---|---|---|---|---|---|---|---|---|---|---|---|---|---|---|---|---|
| 50 | Dicamba-DGA | 5.19 | Fluroxypyr | 3.75 | MCPA 2EHE | Oil | 10.85 | DPM | 16.46 | Aromatic 150ND | 6 | APG 8107U/ | 2.46/ 1.23 | Yes | Yes | Yes | Yes |

TABLE 9-continued

| Example | Water soluble AI | Wt (g) | Water Insoluble AI | Wt (g) | 3rd AI | Oil/Water Soluble (3rd AI) | Wt (g) | Polar Solvent | Wt (g) | Co-solvent | Wt (g) | Surfactants | Wt (g) | 1 | 2 | 3 | 4 |
|---|---|---|---|---|---|---|---|---|---|---|---|---|---|---|---|---|---|
| 51 | Dicamba-DGA | 5.19 | Fluroxypyr meptyl Ester | 3.75 | Bromoxynil Octanoate | Oil | 8.7 | DPM | 13.48 | Aromatic 150ND | 6 | APG 8107U/ Pluronic P105 | 2.46/ 1.25 | Yes | Yes | Yes | Yes |
| 52 | Dicamba-DGA | 5.19 | Fluroxypyr meptyl Ester | 3.75 | MCPA 2EHE/ MCPA amine | Oil/ Water | 5.43/ 14.5 | DPM | 37 | Aromatic 150ND | 6 | APG 8107U/ Pluronic P107 | 2.46/ 1.25 | Yes | Yes | Yes | Yes |
| 53 | Dicamba-DGA | 5.19 | Fluroxypyr meptyl Ester | 3.75 | Pinoxaden | Oil | 1 | DPM | 30.55 | Aromatic 150ND | 6 | None | n/a | Yes | Yes | Yes | — |

Examples 54-56

Following procedures similar to examples 1-3, a series of emulsifiable concentrates were prepared using dicamba DGA (38.5% AE, 56.8% as salt) as water-soluble pesticide and fluoroxypyr meptyl ester as water-insoluble pesticide. The role and amount of water was investigated. The following examples illustrate that, in accordance with the invention, the solvent system quantities of water can be successfully tolerated while still producing a homogenous, single phase product. However, there will be an upper limit of water which will result in phase separation (14.3 wt % in the example given below).

TABLE 10

| Example | Water soluble AI | Wt (g) | Water Insoluble AI | Wt (g) | Polar Solvent | Wt (g) | Wt % water in product | Co-solvent | Wt (g) | Surfactants | Wt (g) | Test 1 | Test 2 | Test 3 |
|---|---|---|---|---|---|---|---|---|---|---|---|---|---|---|
| 54 | Dicamba-DGA | 10.55 | Fluroxypyr meptyl Ester | 7.625 | DPM | 12.05 | 9% | Aromatic 150ND | 12.175 | APG 8107U/ Pluronic P105 | 5/ 2.5 | Yes | Yes | Yes |
| 55 | Dicamba-DGA) | 10.55 | Fluroxypyr meptyl Ester | 7.625 | DPM/ Water | 12.05/ 2 | 12.6% | Aromatic 150ND | 12.175 | APG 8107U/ Pluronic P105 | 5/ 2.5 | Yes | Yes | Yes |
| 56 | Dicamba-DGA) | 10.55 | Fluroxypyr meptyl Ester | 7.625 | DPM/ Water | 12.05/ 3 | 14.3% | Aromatic 150ND | 12.175 | APG 8107U/ Pluronic P105 | 5/ 2.5 | No | — | — |

Wt % water in Example 54 = [10.55 g × (100% − 56.8%)]/(10.55 g + 7.63 g + 12.05 g + 12.18 g + 5 g + 2.5 g) = 4.56 g/49.91 = 9%
Wt % water in Example 55 = {[10.55 g × (100% − 56.8%)] + 2 g}/(10.55 g + 7.63 g + 12.05 g + 12.18 g + 5 g + 2.5 g) = 6.56 g/51.91 = 12.6%
Wt % water in Example 56 = {[10.55 g × (100% − 56.8%)] + 3 g}/(10.55 g + 7.63 g + 12.05 g + 12.18 g + 5 g + 2.5 g) = 7.56 g/52.91 = 14.3%

Examples 57-63

Following procedures similar to examples 1-3, a series of emulsifiable concentrates were prepared using dicamba DGA (38.5% AE, 56.8% as salt) as water-soluble pesticide and fluoroxypyr meptyl ester as water-insoluble pesticide. The role of the co-solvent was investigated. The following examples illustrate that the co-solvent can either be replaced (e.g. Aromatic 200ND can be replaced by Aromatic 150ND) or removed altogether. This emphasizes that the presence of the co-solvent is optional and is not a requirement.

TABLE 11

| Example | Water soluble AI | Wt (g) | Water Insoluble AI | Wt (g) | Polar Solvent | Wt (g) | Co-solvent | Wt (g) | Surfactants | Wt (g) | Test 1 | Test 2 | Test 3 | Test 4 |
|---|---|---|---|---|---|---|---|---|---|---|---|---|---|---|
| 57 | Dicamba-DGA | 0.51 | Fluroxypyr meptyl Ester | 3.05 | DPM | 8.55 | Aromatic 150ND | 4.87 | APG 8107U/ Pluronic P105 | 2.0/ 1.0 | Yes | Yes | Yes | Yes |
| 58 | Dicamba-DGA | 0.51 | Fluroxypyr meptyl Ester | 3.05 | DPM | 8.55 | Aromatic 200ND | 4.87 | APG 8107U/ Pluronic P105 | 2.0/ 1.0 | Yes | Yes | Yes | Yes |
| 59 | Dicamba-DGA | 0.51 | Fluroxypyr meptyl Ester | 3.05 | Hallcomid M-8-10 | 13.42 | — | 0 | APG 8107U/ Pluronic P105 | 2.0/ 1.0 | Yes | Yes | Yes | Yes |
| 60 | Dicamba-DGA | 0.51 | Fluroxypyr meptyl Ester | 3.05 | Hallcomid M-8-10 | 8.55 | Aromatic 150ND | 4.87 | APG 8107U/ Pluronic P105 | 2.0/ 1.0 | Yes | Yes | Yes | Yes |
| 61 | Dicamba-DGA | 0.51 | Fluroxypyr meptyl Ester | 3.05 | Benzyl Alcohol | 13.42 | — | 0 | APG 8107U/ Pluronic P105 | 2.0/ 1.0 | Yes | Yes | Yes | Yes |
| 62 | Dicamba-DGA | 0.51 | Bromoxynil Octanoate | 3.05 | Benzyl Alcohol | 8.55 | Aromatic 150ND | 4.87 | APG 8107U/ Pluronic P105 | 2.0/ 1.0 | Yes | Yes | Yes | Yes |
| 63 | Dicamba-DGA | 0.51 | Bromoxynil Octanoate | 3.05 | Benzyl Alcohol | 8.55 | Aromatic 200ND | 4.87 | APG 8107U/ Pluronic P105 | 2.0/ 1.0 | Yes | Yes | Yes | Yes |

Examples 64-66

Following procedures similar to examples 1-3, a series of emulsifiable concentrates were prepared using dicamba as water-soluble pesticide and bromoxynil octanoate as water-insoluble pesticide. The role of the counter-ion of the herbicidal salt was investigated. The following examples indicate that the counter-ion can be changed while still producing a stable, single phase EC.

TABLE 12

| Example | Water soluble AI | Wt (g) | Water Insoluble AI | Wt (g) | Polar Solvent | Wt (g) | Co-solvent | Wt (g) | Test 1 | Test 2 |
|---|---|---|---|---|---|---|---|---|---|---|
| 64 | Dicamba-DGA aqueous solution (38.5% AE, 56.8% as salt) | 21.1 | Bromoxynil octanoate | 15.25 | DPM | 60 | Aromatic 200ND | 24.35 | Yes | Yes |
| 65 | Dicamba-DMA aqueous solution (30.5% AE) | 6.5 | Bromoxynil octanoate | 1.54 | DPM | 13.46 | — | — | Yes | Yes |
| 66 | Dicamba-K aqueous solution (36% AE) | 6.3 | Bromoxynil octanoate | 1.54 | DPM | 13.46 | — | — | Yes | Yes |

DGA = Diglycolamine
DMA = Dimethylamine
K = Potassium

Examples 67-70

Following procedures similar to examples 1-3, a series of emulsifiable concentrates were prepared using various water-soluble pesticides and propiconazole as water-insoluble pesticide. The role of the water-insoluble a.i. was investigated. The following examples illustrate that the EC of the invention is useful for pesticidal ingredients such as the fungicide propiconazole.

TABLE 13

| Examples | Water soluble AI | Wt (g) | Water Insoluble AI | Wt (g) | Polar Solvent | Wt (g) | Test 1 | Test 2 | Test 3 |
|---|---|---|---|---|---|---|---|---|---|
| 67 | Dicamba-DGA | 2.1 | Propiconazole | 0.52 | DPM | 10 | Yes | Yes | Yes |
| 68 | 2,4-D DMA aqueous solution | 1 | Propiconazole | 0.56 | DPM | 10 | Yes | Yes | Yes |
| 69 | MCPA-DMA aqueous solution | 1 | Propiconazole | 0.53 | DPM | 10 | Yes | Yes | Yes |
| 70 | Dicamba-DMA aqueous solution | 1 | Propiconazole | 0.53 | DPM | 10 | Yes | Yes | Yes |

Examples 71-160

Following procedures similar to examples 1-3, emulsifiable concentrates containing the following combinations of active ingredients (Pesticide 1+Pesticide 2) can also be prepared using routine experimentation:

TABLE 14

| Example | Pesticide 1 (shown in the row opposite) Pesticide 2 (shown in the column below) | Fluroxypyr ester | Bromoxynil ester | MCPA ester | Pinoxaden | Clodinafop | 2,4-D ester | Propiconazole |
|---|---|---|---|---|---|---|---|---|
| 71-77 | Dicamba | X | X | X | X | X | X | X |
| 78-84 | 2,4-D salt | X | X | X | X | X | X | X |
| 85-92 | Clomeprop | X | X | X | X | X | X | X |
| 93-99 | Dichloroprop | X | X | X | X | X | X | X |
| 100-106 | MCPA salt | X | X | X | X | X | X | X |
| 107-111 | MCPB | X | X | X | X | X | X | X |
| 112-118 | Mecoprop | X | X | X | X | X | X | X |
| 119-125 | Mecoprop-P | X | X | X | X | X | X | X |
| 126-132 | Chloramben | X | X | X | X | X | X | X |
| 133-139 | TBA | X | X | X | X | X | X | X |
| 140-146 | Picloram | X | X | X | X | X | X | X |
| 147-153 | Clopyralid | X | X | X | X | X | X | X |
| 154-160 | Aminopyralid | X | X | X | X | X | X | X |

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. A stable, single-phase emulsifiable concentrate, comprising
    (a) a pesticide mixture comprising
        a major amount of at least one water-insoluble pesticide selected from an ester of fluroxypyr and an ester of bromoxynil, and
        a minor amount of at least one water-soluble pesticidal salt, wherein the water-soluble pesticide is selected from a salt of 3,6-dichloro-2-methoxybenzoic acid (dicamba),
        wherein the weight ratio of water-insoluble pesticide to water-soluble pesticidal salt is from 10:1 to 1.01:1;
    (b) a solvent system comprising
        (i) a major amount of a solvent comprising at least one non aqueous polar solvent, wherein the polar solvent is selected from the group consisting of tetrahydrofurfuryl alcohol, dipropyleneglycol monomethylether and mixtures thereof;
        (ii) at least one aromatic hydrocarbon; and
        (iii) water, which is present in an amount up to 12.6% by weight; and
    (c) an emulsifying surfactant system which is effective in forming an oil-in-water emulsion when the emulsifiable concentrate is added to water, wherein the resultant oil-in-water emulsion has a volume-weighted median diameter as measured by diffraction light scattering in excess of 10 nm.

2. The emulsifiable concentrate according to claim 1, wherein the aromatic hydrocarbon comprises a mixture of aromatic hydrocarbons.

3. The emulsifiable concentrate according to claim 1, wherein the ester of fluroxypyr is fluroxypyr meptyl ester.

4. The emulsifiable concentrate according to claim 1, wherein the ester of bromoxynil is bromoxynil octanoate.

5. The emulsifiable concentrate according to claim 1, wherein the water-insoluble pesticide further includes at least one pesticide selected from the group consisting of pinoxaden, fenoxaprop-p, clodinafop and propiconazole.

6. The emulsifiable concentrate according to claim 1, wherein the dicamba salt is selected from the group consisting of sodium, potassium, ammonia, dimethylamine, diethylamine, triethylamine, monoethanolamine, diethanolamine, 2-hydroxyethylammonium, aminoethoxyethanol, triisopropanolamine, tris(2-hydroxypropyl)amine, aminopropylmorpholine and triethanolamine.

7. The emulsifiable concentrate according to claim 6, wherein the dicamba salt is the aminoethoxyethanol salt of dicamba.

8. The emulsifiable concentrate according to claim 1, wherein the polar solvent has a Hansen polarity parameter greater than 2.

9. The emulsifiable concentrate according to claim 1, wherein the water content is greater than 3% by weight of the composition.

10. The emulsifiable concentrate according to claim 1, wherein the emulsifying surfactant system comprises at least one alkyl polyglycoside surfactant.

11. The emulsifiable concentrate according to claim 1, wherein the emulsifying surfactant system comprises at least one alkylene oxide surfactant.

12. The emulsifiable concentrate according to claim 1, wherein the emulsifying surfactant system comprises a mixture of at least one alkyl polyglycoside and at least one propylene-oxide/ethylene-oxide copolymer.

13. A method for controlling weeds in crops of useful plants, said method comprising treating the plants, plant parts or locus thereof with a herbicidally effective amount of an EC composition according to claim 1 or a dilute herbicidal spray composition or oil-in-water emulsion formed when the EC composition is added to an aqueous liquid carrier.

* * * * *